(12) United States Patent
Schirmeister et al.

(10) Patent No.: US 7,981,830 B2
(45) Date of Patent: Jul. 19, 2011

(54) CATALYST-COATED SUPPORT, METHOD FOR PRODUCING THE SAME, REACTOR COMPRISING THE SAME AND USE THEREOF

(75) Inventors: Steffen Schirmeister, Mühlheim An Der Ruhr (DE); Karsten Büker, Dortmund (DE); Martin Schmitz-Niederau, Münster (DE); Bernd Langanke, Holzwickede (DE); Andreas Geisselmann, Offenbach (DE); Georg Markowz, Kahl (DE); Klaus Thomas Schwarz, Frankenberg (DE); Elias Johannes Klemm, Nürnburg (DE); Frank Becker, Offenbach (DE); Reinhard Machnik, Rodenbach (DE)

(73) Assignees: Uhde GmbH, Dortmund (DE); Evonik Degussa GmbH, Düsseldorf (DE)

( * ) Notice: Subject to any disclaimer, the term of this patent is extended or adjusted under 35 U.S.C. 154(b) by 552 days.

(21) Appl. No.: 11/912,031

(22) PCT Filed: Apr. 18, 2006

(86) PCT No.: PCT/EP2006/003502
§ 371 (c)(1),
(2), (4) Date: May 28, 2008

(87) PCT Pub. No.: WO2006/111430
PCT Pub. Date: Oct. 26, 2006

(65) Prior Publication Data
US 2008/0286176 A1   Nov. 20, 2008

(30) Foreign Application Priority Data

Apr. 22, 2005 (DE) .......................... 10 2005 019 000

(51) Int. Cl.
*B01J 23/00* (2006.01)
*B01J 8/02* (2006.01)
(52) U.S. Cl. ........ 502/300; 502/330; 502/305; 502/313; 502/325; 502/328; 502/353; 422/211
(58) Field of Classification Search .................. 422/211; 502/300, 305, 313, 325, 328, 330, 353
See application file for complete search history.

(56) References Cited

U.S. PATENT DOCUMENTS 4,305,843 A   12/1981   Krabetz et al.
(Continued)

FOREIGN PATENT DOCUMENTS

DE   2745100 C2   4/1978
(Continued)

OTHER PUBLICATIONS

Aartun, I., et al "Catalytic conversion of propane to hydrogen in microstructured reactors", Chemical Engineering Journal, 2004, vol. 101, pp. 93-99.
(Continued)

*Primary Examiner* — Walter D Griffin
*Assistant Examiner* — Huy-Tram Nguyen
(74) *Attorney, Agent, or Firm* — Connolly Bove Lodge & Hutz LLP

(57) ABSTRACT

Supports having a catalytic coating comprising at least one porous and cavity-containing catalyst layer are described, cavities being irregular spaces having dimensions greater than 5 µm in at least two dimensions or having cross-sectional areas of at least 10 µm². The catalytic coatings are distinguished by a high adhesive strength and can preferably be used in microreactors.

42 Claims, 3 Drawing Sheets

U.S. PATENT DOCUMENTS

| | | | |
|---|---|---|---|
| 4,744,888 A | 5/1988 | Hung et al. | |
| 5,164,078 A | 11/1992 | Hung et al. | |
| 5,316,661 A | 5/1994 | Dessau et al. | |
| 5,846,899 A | 12/1998 | Kumazawa et al. | |
| 5,980,843 A | 11/1999 | Silversand et al. | |
| 6,197,365 B1 | 3/2001 | Bachinger et al. | |
| 6,720,171 B2 | 4/2004 | Schunk et al. | |
| 7,008,996 B2 | 3/2006 | Furuta et al. | |
| 7,179,430 B1 * | 2/2007 | Stobbe et al. | 422/180 |
| 2002/0028164 A1 | 3/2002 | Schutte et al. | |
| 2004/0086637 A1 | 5/2004 | Chung et al. | |
| 2006/0276334 A1 | 12/2006 | Balduf et al. | |
| 2007/0266896 A1 * | 11/2007 | Suwa et al. | 106/287.16 |

FOREIGN PATENT DOCUMENTS

| | | | |
|---|---|---|---|
| DE | 2752811 A1 | 5/1979 | |
| DE | 7323023 U1 | 2/1981 | |
| DE | 7640618.3 U1 | 12/1982 | |
| DE | 3324935 A1 | 1/1984 | |
| DE | 19839782 A1 | 3/2000 | |
| DE | 19959973 | 6/2001 | |
| DE | 10042746 A1 | 3/2002 | |
| DE | 69706346 T2 | 6/2002 | |
| DE | 10110465 A1 | 10/2002 | |
| DE | 10313317 A1 | 11/2003 | |
| DE | 69906741 T2 | 12/2003 | |
| DE | 10335510 A1 | 3/2005 | |
| EP | 1043068 | 10/2000 | |
| GB | 1094256 | 12/1967 | |
| GB | 1238444 | 7/1971 | |
| GB | 1586314 | 3/1981 | |
| GB | 2123711 | 2/1984 | |
| WO | WO-98/02242 A1 | 1/1998 | |
| WO | WO-03/033146 A1 | 4/2003 | |
| WO | WO-2005/011858 A1 | 2/2005 | |

OTHER PUBLICATIONS

Nijhuis, T. A., et al., "Preparation of monolithic catalysts", Catalysis Reviews, 2001, vol. 43, No. 4, pp. 345-380.

Falbe, J., et al., "Chemie", Römpp Lexikon, 3536-3527.

* cited by examiner

CATALYST-COATED SUPPORT, METHOD FOR PRODUCING THE SAME, REACTOR COMPRISING THE SAME AND USE THEREOF

RELATED APPLICATIONS

This application is a national stage application (under 35 U.S.C. §371) of PCT/EP2006/003502, filed Apr. 18, 2006, which claims benefit of German application 10 2005 019 000.6, filed Apr. 22, 2005.

The present invention relates to a supported catalyst layer having good adhesive strength and high planarity and low tolerance of the layer thickness, a process for the production thereof, the use thereof in heterogeneously catalyzed processes and a reactor which contains such a catalyst layer.

Many chemical reactions are heterogeneously catalyzed in a very wide range of reactors. Reactors equipped with catalytic layers have long been known.

DE 76 40 618 U describes a process for the catalytic purification of exhaust gases, in which a metal tube which is formed so as to disturb flow and is lined with catalyst material is used. In addition to the direct application of the catalyst from the liquid phase or gas phase, the impregnation of a porous layer applied in the metal tube with catalytically active material is described. This publication also suggests first applying a firmly adhering layer, for example of alpha-alumina, to the metal tube and directly applying the catalyst thereafter altogether with the firmly adhering layer.

DE 198 39 782 A1 discloses a metallic reaction tube having a catalytic coating containing a multimetal oxide material, which reaction tube can be used in catalytic gas-phase reactions. The catalytic layer is applied in the form of a solution, emulsion or dispersion directly to a metallic reaction tube without adhesion-promoting intermediate layer. This can be effected by spraying or immersion. Typical layer thicknesses are in the range of from 10 to 1000 μm. For the production of thicker layers multiple coating of the reaction tube is recommended.

DE 199 59 973 A1 describes the process for the production of arrays of heterogeneous catalysts composed of a body which has continuous channels in which different catalysts are applied. The process is said to extend the known spectrum of arrays. The process can be automated.

It is known that sheet-like catalyst layers can be applied by immersing metallic or ceramic honeycomb bodies for coating in a washcoat suspension. Either a catalytic component is already present in the washcoat or said component is applied subsequently by impregnation. This is followed by drying, calcination and optionally reduction. Such a process is described, for example, in Catal. Rev. 2001, 43, 345-380.

DE 699 06 741 T2 discloses a porous diesel exhaust gas filter, a flow-through filter body having a honeycomb wall structure being used, the surface of which body is coated with catalytically active material. A surface area-increasing coating is applied to the filter body by coating with a washcoat, for example by applying a sol comprising small colloidal particles to the calcined filter body. A catalytically active metal layer can then be applied, for example, by impregnating the filter body with a metal slurry.

U.S. Pat. No. 5,316,661 describes a process for the crystallization of a zeolite layer on a substrate.

WO-A-03/33,146 discloses supported catalysts for the selective oxidation of carbon monoxide. These have a catalyst layer which is applied, above an adhesion-promoting layer of a crystalline silicate and silica particles, to a metallic support. The adhesion-promoting layer is produced on the metallic support by applying an aqueous mixture of crystalline silicate and silica sol.

EP-A-1,043,068 discloses a process for the preparation of a supported catalyst, in which a catalyst-containing material is mixed with a solvent and is deposited, by spraying, on a substrate heated to above the boiling point of the solvent. The process permits targeted deposition of the catalyst material with large active surface area and good adhesive strength on a substrate.

DE-A-103 35 510 describes coated catalysts support bodies which have high adhesive strength and are characterized by the occurrence of cracks and a large total crack length. According to the description, most of these cracks end at the surface of the catalyst layer. The occurrence of cavities and other porous spaces in the catalyst layer is not described.

Recently, microreactors comprising catalytic wall elements having a wall spacing of <1 mm have been proposed. Examples of these are described in DE 100 42 746 A1 and DE 101 10 465 A1.

In these wall reactors, a reaction mixture is passed through between in each case two catalytically coated plate-like wall elements arranged in parallel. Usually, such a reactor consists of a series of wall elements. Owing to the small spacing of the wall elements, a large wall-to-volume ratio is achieved, which ratio permits a high heat removal rate and a procedure with reaction mixtures which are explosive under normal conditions. The high heat removal rate permits very good temperature control while avoiding so-called hot spots in highly exothermic reactions. Wall reactors can therefore be operated at a higher temperature than in the case of the polytropic procedure. As a result of this, higher space-time yields can be achieved in catalytic wall reactors. Further undesired effects of hot spots, such as loss of selectivity and deactivation, can also be circumvented. Owing to the good heat transport, it is also possible in particular to use active catalysts whose evolution cannot be controlled in conventional reactors.

In the known reactors, catalytic wall elements consisting of a plate with apparatuses for fastening and sealing are already used. On the reaction side, the plate has one or more flat catalyst-coated sheet-like elements. The back of the plate may have a varied design and often channels for cooling of heating medium are expedient.

For such microreactors and other wall reactors there is a need for particularly firmly adhering catalyst layers having a uniform layer thickness and low resistances to material transport.

The known processes and catalyst layers produced therewith are still in need of improvement in many respects. Thus, known processes frequently require the use of special combinations of substances or the achievable layer thickness tolerances and/or adhesive strengths are unsatisfactory.

In particular, catalyst layers which can be industrially used have to meet the following requirements:
  the layers must have sufficient adhesive strength to avoid flaking during installation and during operation
  the stability of the layers must be ensured even after being subjected to thermal stress at reaction temperature or during any calcination required for decomposing catalyst precursors
  the layer thickness must be as uniform as possible so that the flow velocity in the reactor is virtually constant over the reactor width and reactor length; this criterion plays an outstanding role particularly in the case of microreactors the layer thickness must be sufficiently great in order to introduce sufficient catalytically active material into the reactor; typical layer thicknesses are from 20 μm to 3 mm the catalyst layer must have sufficient catalytic activity, i.e. sufficiently large internal surface area and porosity the resistance to material transport in the catalyst layer must be sufficiently low.

It is an object of the present invention to provide a catalyst layer which meets these requirements.

A further object of the present invention is the provision of a process by means of which catalyst layers having good adhesive strength and high porosity and low tolerance of the layer thickness and having low resistance to material transport can be produced in a simple and economical manner and which can be used universally with a large number of catalyst systems.

The invention relates to a support having a catalytic coating comprising at least one porous catalyst layer which has cavities. In the context of the present description, cavities are understood as meaning irregular spaces having dimensions greater than 5 μm in at least two dimensions or having cross-sectional areas of at least 10 μm².

These spaces are substantially closed and are substantially connected to the layer surface or further cavity only by pores having diameters of less than 5 μm or by cracks having a width of less than 5 μm. Cavities can be recognized in scanning electron micrographs of sections of catalyst layers impregnated with resin. The cross-sectional area of the dimensions can be determined by methods known per se, for example by quantitative microscopy. In the context of this invention, irregular spaces are understood as meaning spaces having aspherical and/or acylindrical geometry which greatly deviates from the ideal spherical and/or cylindrical shapes and whose internal surface consists of local roughnesses and macropores. In contrast to cracks, these cavities do not have a unique preferred direction.

Cavities are a part of the pore system. They are particularly large macropores. In the context of the IUPAC definition, macropores are pores having a diameter greater than 50 nm.

The proportion of cavities in the catalyst layer is preferably chosen so that the visible area fraction of the cavities in a representative sectional image is from 2 to 60%, preferably from 3 to 50% and very particularly preferably from 5 to 35%, areas greater than 10 μm² which are visible in the sectional image being rated as cavities. The contrast and the resolution in the image evaluation should be chosen so that exclusively spaces—detectable in layers comprising cast resin from a particularly dark contrast—and no layer material, and no pores or cracks emanating from the cavities and having diameters of less than 5 μm are detected. In case of doubt, the arithmetic mean of the area fractions of five randomly selected sectional images distributed over the layer should be used in the case of inhomogeneous layers in the context of the present description.

Surprisingly, in spite of substantially reduced material density and hence reduced contact area of the layer-forming particles, such cavity-rich layers have particularly high adhesive strengths. Without being tied to one theory, the inventors attribute this to two active effects:

1. The cavities prevent the propagation of cracks within the layer and thus help to reduce mechanically or thermally induced stresses, as result during installation of the catalyst or during operation. In micrographs of sections, it is evident that cracks occurring in the layer end in cavities and "die out" (cf FIG. 1). In the case of cavity-free layers such cracks run through the entire layer and lead to mechanical instability (cf. FIG. 2)

2. The cavities promote the removal of the solvent or suspending media in the drying process during the coating and thus prevent the pressure build-up which leads to mechanical damage to the layer.

The layers according to the invention exhibit high adhesive strengths also after mechanical and thermal loading. These advantages result in low sensitivity during the handling and use of the catalyst layer, such as, for example, during installation and operation. Typically, these layer systems exhibit adhesive strengths of >1 kPa (measured on the basis of DIN EN ISO 4624), in particular >10 kPa and very particularly >50 kPa.

In addition to the cavities, the catalyst layer according to the invention preferably has further macropores of smaller diameter in a high proportion.

In a preferred embodiment, the catalyst layer contains a pore system in which at least 50%, preferably at least 70%, of the pore volume are formed by macropores having a diameter of at least 50 nm. Pore volume is understood as meaning that volume in pores having a diameter greater than 4 nm which can be measured by means of mercury porosimetry according to DIN 66133. A contact angle of 140° and a surface tension of 480 mN/m for mercury are assumed. For the measurement, the sample is dried at 105° C. The proportion of the pore volume in macropores is likewise determined by mercury porosimetry.

The high proportion of macropores according to the particularly preferred embodiment is the cause of the low resistance to material transport within the catalyst layer. It is this which actually permits the use of thicker layers without sacrificing selectivity and activity. Thicker layers have the advantage of providing more catalyst material per unit area. The costs, in particular of a microreactor, increase with the area requirements and consequently potential cost reductions result from thicker layers.

The combined pore and cavity volume of a catalyst layer, which can be determined by saturating water absorption and differential weighing, is typically from 30 to 95%, preferably from 50 to 90%, based on the total volume of the layer.

In a further preferred embodiment, the support coated according to the invention has a uniform layer thickness with a tolerance of, preferably, less than ±30 μm.

Because of the uniform layer thickness and due to uniform axial and lateral flow conditions, a narrow residence time distribution in the reactor can be established. This leads to optimum selectivities and an optimum space-time yield.

The supports may have any desired geometry and may consist of a very wide range of materials. Thus, they may be, for example, tubes. Sheet-like bodies are preferably used, in particular plates. Sheet-like bodies which have sheet-like depressions to which the catalyst layers are applied or which have grooves in addition to sheet-like depressions are particularly preferably used.

A further development of the supports comprises so-called heat-exchange plates. These are understood as generally meaning at least two metal sheets which are arranged parallel in at least some cases and are connected to one another in point-like contact regions, for example by welding or soldering, and are a distance apart outside these contact regions. Owing to this structure, heat-exchange plates have a cushion-like structure, a network-like channel pattern being formed between those surfaces of the metal sheets which are connected to one another via the contact regions and face one another. This channel pattern can firstly serve as a reaction space treated with a catalyst, and secondly coolant can be passed through said channel pattern. Heat-exchange plates are described, inter alia, in DE-A-101 08 380 and DE-C-100 11 568 and are commercially available from DEG Intense Technologies & Services GmbH, Germany.

The support substrate preferably consists of metallic or ceramic materials. For example, the support may consist of an aluminum-, iron-, copper- or nickel-containing metal or of a metal alloy; or it may consist of ceramics, such as, for example, of alumina, titanium oxide or silica, zirconium oxide, silicon carbide or cordierite.

The support substrate may have any desired surface. In addition to smooth surfaces, roughened or porous surfaces may also be used. The surface may consist of the material of the support substrate or of a layer of additionally applied material, for example an oxide layer.

The thickness of the catalyst layer may cover a wide range depending on the application; it is typically from 50 to 3000 µm, preferably from 200 to 1000 µm, it being possible for the catalyst layer to be composed of individual layers which may have identical or different compositions.

Very particularly preferred supports are those in which the catalyst layer comprises an adhesion-promoting layer which is applied directly to the surface of the support and which may have no catalytic action. Typical thicknesses of this adhesion-promoting layer are less than 100 µm, preferably from 100 nm to 80 µm.

Particularly preferred adhesion-promoting layers exhibit a matrix which is substantially homogeneous in the micron range and preferably contain no individual structures of more than 5 µm in diameter, as may form, for example, with the use of coarser particles in a suspension for application to the support. In contrast to the catalytic top layer, the adhesion-promoting layer has no cavities.

At least one macroporous layer of catalytically active material which has structures having a diameter of more than 1 µm is applied to this first layer.

The material of the first adhesion-promoting layer may be of any desired one, provided that it does not change under the reaction conditions under which the catalyst layer is used. Said material may comprise typical binder materials, such as inorganic oxides and/or heat-stable plastics. The first layer may also contain a catalyst.

Examples of materials of which the first adhesion-promoting layer consists are silica, alumina, zirconium oxide, titanium oxide and mixtures thereof.

At least one further layer containing cavities is applied to the first adhesion-promoting and cavity-free layer. However, layers containing cavities can also be applied directly to the support, without the adhesion-promoting layer. The cavity-containing layer typically contains structures which are attributable to particles having a diameter of more than 1 µm and comprise catalytically active material and optionally further, inert material.

The catalytic materials may be widely chosen. Of particular interest are catalyst systems for strongly exothermic or endothermic reactions, in particular for oxidation reactions. For example, the following may be mentioned as basic systems to be varied with promoters:

noble metals supported on ceramic or active carbon
multimetal oxides which consist of a selection of the oxides of molybdenum, bismuth, vanadium, tungsten, phosphorus, antimony, iron, nickel, cobalt and copper as base bodies in addition to further dopants
zeolites, such as, for example, molecular sieves based on titanium-containing molecular sieves of the general formula $(SiO_2)_{1-x}(TiO_2)_x$, such as titanium silicalite-1 (TS-1) having an MFI crystal structure, titanium silicalite-2 (TS-2) having an MEL crystal structure, titanium beta-zeolite having a BEA crystal structure and titanium silicalite-48 having the crystal structure of zeolite ZSM 48.
Fischer-Tropsch catalysts, in particular based on Co or Fe Fe-, Ni-, Co- or Cu-based catalysts
solid bases or acids
mixtures of these systems The following catalyst systems are particularly preferably used:

titanium silicalite-1
metals of group VIII B of the Periodic Table of the Elements, preferably of the platinum metals, in particular Pd, combined with metals of group I B of the Periodic Table of the Elements, preferably with Au and an alkali metal salt preferably of an organic acid, very preferably potassium acetate, and optionally further promoters in an oxidic support matrix, preferably an oxide having a high proportion of silica
metals of the group VIII B of the Periodic Table of the Elements, preferably of the platinum metals, in particular Pd, combined with metals of group II B of the Periodic Table of the Elements, preferably with Cd and an alkaline metal salt preferably of an organic acid, very preferably potassium acetate, and optionally further promoters in an oxidic support matrix, preferably in an oxide having a high proportion of silica
mixtures of the oxides and mixed oxides of Mo, Bi, Fe, Co, Ni and optionally further additions, e.g. alkali metals, such as K
mixtures of the oxides and mixed oxides of Mo, V, Cu, W and optionally further additions, e.g. elements of group V A of the Periodic Table of the Elements, preferably Sb and/or metals of group V B of the Periodic Table of the Elements, preferably Nb
Ag on an alumina which is preferably at least partly in the alpha-phase and optionally further additions, such as, for example, alkali metals, such as Cs, and/or metals of the group VII B of the Periodic Table of the Elements, such as Re
vanadium pyrophosphates and optionally further additions
vanadium oxide on an oxidic support and optionally further additions
metals of group VIII B of the Periodic Table of the Elements, preferably of the platinum metals, in particular Pd and/or Pt on an alumina.

The catalytically active materials may be present in an inert or supporting matrix of inorganic oxides or heat-stable plastics.

Preferred materials of this matrix are oxides of Si, Al, Ti, Zr and/or mixtures thereof. In each case further doping elements and other secondary components customary for the production of catalyst layers may also be present. Examples of such materials are, among many others, alkali metal and alkaline earth metal compounds, in particular alkali metal and alkaline earth metal halides, phosphates and sulfates.

The thickness of the catalytically active layer is particularly uniform, viz the layer is distinguished by a high planarity and a low tolerance in layer thickness. This is demonstrated by measurements of the layer thickness with the whirl pool principle according to DIN EN ISO 4287 which show low standard deviations of <35 µm, preferably <25 µm, with a multitude of measurements. However the local roughness is relatively high. This local roughness does not affect the distribution of critical residence times over the gap width and improves mass transport between head space and catalyst layer as the formation of at least partially tubulent flow in the head space is improved. The microscope reveals a particularly open structure of the surface, which ensures good penetration of the reactants. This open pore structure is formed, according to the invention, by open, that is non-closed preforms of cavities having dimensions greater than 5 µm in at least two dimensions, which are present on the layer surface. The inner surfaces of these open structures directed towards the support possess pores which run into the interior of the catalytically active layer and thus ensure the mass transport into the catalyst layer. Furthermore, individual connections between the open structures occurring on the surface and the closed cavities present in the interior of the catalytic layer via macroporous channels may be present and/or individual connections between closed cavities within the catalytically active layer may be present.

The local roughness is demonstrated in a profilogramme which can be recorded by means of a probe and shows a high number of maxima, minima and zero crossings per unit length as well as a high roughness depth. The layers are further distinguished by especially exact and narrow peaks. When determining the topography with a probe according to DIN EN ISO 4287 the average number of zero line passages is typically in the range of >2 per mm, preferably >2.5 per mm and most preferably 3-8 per mm (measured with Form Talysurf Series 2, Taylor-Hobson Precision), given that the length of the measured section is sufficient. A zero line passage is defined by the intersection point of the profile with the centerline. The roughness depth measured by a probe and determined according to DIN EN ISO 4287 is >70 µm, preferably >100 µm, and most preferably >120 µm with an overall measured length of 40 mm and a single measured length of 8 mm taken as a basis.

Non-inventive catalyst layers, which can be obtained for example by known spray processes and by doctor blade processes, generally show larger variations of layer thickness but these do not show the favourable local roughness. Coating processes which are known to result in a precise adjustment of layer thickness, such as CVD, are very elaborate and show structures with local smoothness.

The roughness of the surface can optionally be reduced by an aftertreatment, such as grinding and polishing.

The support according to the invention which has a catalytic coating can be produced by a particularly simple and economical process. This is likewise a subject matter of the present invention.

The process comprises the measures:
a) initial introduction of a support substrate,
b) optional application of an adhesion-promoter layer,
c) spraying on of a suspension having a solids content of at least 30% by weight, containing particles of catalytically active material having a median diameter ($D_{50}$ value) of at least 5 µm (determined by laser diffraction in suspension) and/or the precursor thereof and optionally further constituents of catalytically active layers, and
d) optionally one or more repetitions of step c).

The process is carried out in such a way that coalescing of the sprayed-on suspension on the support substrate is substantially prevented. In other words, the moisture content of the drops at the time of contact is chosen so that on the one hand a sufficiently high viscosity prevents free coalescence but on the other hand the drops have a sufficiently high aggregation power to bind firmly to the layer underneath. This can be checked under the optical microscope; coalesced layers have a smooth surface whereas, in the process according to the invention, a structure which is rough on the micron scale and has orifices and valleys is produced.

With this proviso, the person skilled in the art can choose a window which permits such a spraying result from the parameters of solids content, mass flow, spraying distance, droplet size and substrate and suspension temperature.

During spraying, it is preferable to use a nozzle technique which permits good focusing of the spray jet so that the overspray, i.e. the material loss due to sprayed material striking next to the support or parts of the support which are not to be coated is minimized. For example, the HVLP nozzle technique in which the spray cone can be limited by additional compressed-air nozzles is suitable here.

In a particular embodiment, the support substrate is at elevated temperature but below the boiling point of the suspending medium during the coating. The preferred temperature in the case of aqueous suspensions is 30-80° C.

In a further preferred embodiment, the particles of the suspension have a broad particle size distribution with a span $D_x=(D_{90}-D_{10})/D_{50}>1.5$. Here, $D_x$ designates the particle diameter of the largest particle in the volume fraction of the smallest particles with a volume fraction of x% of the total particle volume.

In a further preferred embodiment, the particles of the suspension have a rough surface and an irregular shape, as formed, for example, by milling or crushing.

In a further preferred embodiment, a binder is added to the suspension. Suitable binders are inorganic or organic materials and mixtures thereof.

In particular, sols, very finely divided suspensions or solutions of the oxides of Al, Si, Ti, Zr or mixtures thereof can be used as inorganic binder materials. Further preferred inorganic binders are very finely divided oxides having a median particle size ($D_{50}$ value) of <2 µm, such as, for example, pyrogenic oxides or very finely milled precipitated oxides, mechanical crosslinking agents, such as glass fibers or special acicular or rod-like crystallites, such as, for example, Actigel™ 208 (manufacturer ITC-Floridin).

Organic binder materials which may be used are in particular polyalcohols, such as, for example, glycerol, ethylene glycol or polyvinyl alcohol, PTFE, polyvinyl acetate, cellulose derivatives, such as methylcellulose or cellulose fibers.

A preferred variant of the process according to the invention comprises the optional part-step b), the spraying on of a first suspension containing nanoparticulate material without particles having diameters of more than 5 µm onto the surface of the support in an amount such that a first adhesion-promoting layer having a thickness of up to 80 µm, preferably 5-30 µm, forms.

In a further variant, the process according to the invention comprises the step a) defined above, the optional step b) and c') the spraying on of a suspension having a solids content of at least 30% by weight, containing particles of inert and/or catalytic materials having a median diameter ($D_{50}$ value) of at least 5 µm (determined by laser diffraction in suspension) and optionally further constituents of catalytically active layers, and d') optionally one or more repetitions of c') and, as step e) after the production of such a layer system, the impregnation thereof with catalytically active materials and/or precursors thereof and/or promoter materials and/or precursors thereof.

After the spraying on of the individual layers or of the total layer system or parts thereof, these can optionally be dried and/or calcined before further treatments of the layers are effected.

By means of calcination, for example at a temperature of from 250 to 1200° C., organic or other decomposable residues can be removed. The pretreatment may consist in a combination of these individual processes which is variable with respect to the sequence.

The support substrate used in the process according to the invention can optionally be pretreated before the coating, in particular by roughening of the support substrate surface which is to be coated with catalyst, by mechanical, chemical and/or physical methods. This pretreatment may lead to a further improved adhesion of the layers to be applied to the support. This is advisable, in particular for metallic supports. Thus, the support substrate surface to be coated can be roughened by mechanical methods, such as sand blasting or grinding, or by chemical methods, such as etching with acids or bases. Grease residues can be removed by solvents.

The catalyst suspension to be sprayed on contains at least one or more catalytically active materials or precursors thereof.

Precursors may be, for example nitrates, oxalates, carbonates, acetates or other salts which can be converted, into oxides by thermal or oxidative decomposition.

The catalytically active materials or precursors thereof may be present in molecular, colloidal, crystalline and/or amorphous form. The actual catalyst materials or precursors thereof may be present in the suspension or may be subsequently applied by impregnation.

Acids or bases can be added for establishing the pH. Furthermore, organic constituents, such as surfactants, binders or pore formers, may be present. A suitable suspending medium or solvent is in particular water. However, organic liquids may also be used. This suspension to be applied is applied by spraying or atomizing. Parts which are not to be coated can be covered or masked.

Commercial airless high-pressure nozzles or binary nozzles can be used for the spraying, it being possible for jet guidance to be effected manually or preferably automatically. In the automated procedure, it is advisable to move the nozzle under computer control over the surface to be sprayed and to monitor and adjust specifically the application of the material and further parameters of the method.

The spraying on of the individual layers can be effected in a manner known per se, a large number of parameters of the method being available to the person skilled in the art. Examples of these are the spray pressure, the spraying distance, the spray angle, the advance velocity of the spray nozzle or, in the case of a stationary spray nozzle, of the substrate, the nozzle diameter, the material flow rate and the geometry of the spray jet. Furthermore, the properties of the suspensions to be sprayed may influence the quality of the resulting layers, for example, density, dynamic viscosity, surface tension and zeta potential of the suspension used.

For the production of the support coated according to the invention, a stepwise application is effected. It may furthermore be advantageous to heat the support material at least during the spraying on of the first suspension but advantageously during the application of all layers. The support is preferably heated to a temperature below the boiling point of the solvent used.

After the application of the respective layer one or two thermal treatments for drying and calcination can be effected. If the applied layer has not already dried, a separate drying, for example at temperatures of 20-200° C., or drying in combination with a calcination, for example at temperatures of 200-1000° C., may be effected. The drying and the calcination can be carried out in an oxidizing atmosphere, for example in air, or in an inert atmosphere, for example in nitrogen.

It is also possible first to apply all layers and then to dry and to calcine the layer system.

When spraying on a plurality of layers containing catalytically active material, these may have the same composition; in this case, the same suspension is therefore always used after the optional application of an adhesion-promoter layer. However, it is also possible to produce layers containing catalytically active material having a different composition or some layers consisting of inert material.

On application of the individual layers, as far as possible planer layers having a low tolerance of the total layer thickness of ±25 μm can preferably be produced so that no further processing is necessary. However, it is also possible to smoothen applied layers, for example by grinding the surface of the layer system produced or by milling, for example using CNC machines.

After the drying or calcination, optionally further catalytic components or precursors thereof can be applied by impregnation. For reasons relating to work safety and economics, it is generally advisable to carry out such an impregnation only after any final mechanical treatment. For this purpose, the support layer is coated with the solution or suspension containing the components or immersed in said solution or suspension or sprayed. The impregnation may be followed by drying and/or calcination.

The supports coated according to the invention can be used in a very wide range of reactors, for example in plate-type or tubular reactors.

The invention furthermore relates to a reactor containing at least one of the supports according to the invention which have a catalytic coating.

The supports according to the invention are preferably used in wall reactors, which also include microreactors. In the context of this description, microreactors are to be understood as meaning those reactors in which at least one of the dimensions transverse to the direction of flow of the reaction space or of the reaction spaces is less than 10 mm, preferably less than 1 mm, particularly preferably less than 0.5 mm.

Wall reactors and in particular microreactors have a plurality of reaction spaces, preferably a plurality of reaction spaces parallel to one another.

The dimensioning of the reaction spaces may be arbitrary, provided that at least one dimension is in the region of less than 10 mm.

The reaction spaces may have round, ellipsoidal, triangular or polygonal, in particular rectangular or square, cross sections. The or one dimension of the cross section is preferably less than 10 mm, i.e. at least one side length or the or a diameter.

In a particularly preferred embodiment, the cross section is rectangular or round and only one dimension of the cross section, i.e. one side length or the diameter, is in the region of less than 10 mm.

The material enclosing the reaction space may be arbitrary provided that it is stable under the reaction conditions and permits sufficient heat removal and the surface of the reaction space is completely or partly coated with the layer system according to the invention, containing catalytically active material.

The present invention therefore also relates to a reactor which can be used in particular for the heterogeneously catalyzed gas-phase reaction, comprising:
i) at least one reaction space of which at least one dimension is less than 10 mm, and
ii) the surface of the reaction space is coated or partly coated with the above-defined layer system containing catalytically active material.

A preferred microreactor is one which has a large number of spaces which are arranged vertically or horizontally and parallel and which have at least one feed line and one discharge line each, the spaces being formed by stacked plates or layers, and some of the spaces being reaction spaces of which at least one dimension is in the region of less than 10 mm, and the other spaces being heat transport spaces, the feed lines to the reaction spaces being connected to at least two distributor units and the discharge lines from the reaction spaces being connected to at least one collecting unit, the heat transport between reaction spaces and heat transport spaces being effected by at least one common space wall which is formed by a common plate.

A particularly preferably used microreactor of this type has spacer elements arranged in all spaces, contains catalyst material applied at least partly by the process according to the invention on the inner walls of the reaction spaces, has a hydraulic diameter, which is defined as the quotient of four times the area to the circumferential length of the free flow cross section, in the reaction spaces of less than 4000 μm, preferably less than 1500 μm and particularly preferably less than 500 μm, and a ratio of the smallest perpendicular distance between two adjacent spacer elements to the slot height of the reaction space after coating with catalyst of less than 800 and greater than or equal to 10, preferably less than 450 and particularly preferably less than 100.

The invention furthermore relates to the use of the supports described in a reactor for reacting organic compounds. These may be reactions in the gas phase, in the liquid phase or in a phase having a supercritical state.

The reactor is preferably a wall reactor, particularly preferably a microreactor.

The reaction of organic compounds is preferably a strongly exothermic or endothermic reaction (magnitude of ΔH greater than 50 kJ/mol)

Examples of reactions are oxidation and ammoxidation reactions, for example:
  epoxidation of olefins, such as the oxidation of propene to propene oxide or of ethylene to ethylene oxide or of allylchloride to epichlorohydrin
  oxidative coupling of acetic acid and ethylene to give vinyl acetate
  oxidation of ethane and/or ethene to give acetic acid
  oxidation of propene to acrolein
  oxidation of propene and/or acrolein to give acrylic acid
  oxidation of propane to give acrolein and/or acrylic acid
  oxidation of butane to give formic acid or to give acetic acid
  oxidation of isobutane and/or isobutene to give methacrolein and/or methacrylic acid
  oxidation of xylene and/or naphthalene to give phthalic anhydride
  oxidation of butane and/or butene to give maleic anhydride
  ammoxidation of propene to give acrylonitrile
  ammoxidation of aromatics to give benzonitriles Further examples of reactions are hydrogenation reactions of organic compounds, for example the hydrogenation of aromatics and of nitro compounds and the selective hydrogenation of unsaturated organic compounds.

Further reactions of interest are reactions of synthesis gas, such as, for example, Fischer-Tropsch reaction and methanol synthesis, or condensation reactions, such as the conversion of acetone to isophorone.

The invention is described below with reference to working examples:

EXAMPLE 1

Wall Catalyst TS-1 on Aluminum 99.5

A 1.0 mm deep and 20 mm wide groove was cut in each case in the middle of three 100 mm long, 30 mm wide and 3 mm thick plates of aluminum (Al 99.5). The plates were pickled for 30 min at room temperature in a nitric acid solution, passivated with a hydrogen peroxide solution after washing with demineralized water, and then washed again with demineralized water. After drying, the webs of the plates were covered with adhesive tape and preheated in a drying oven to 50° C.

At the same time, a suspension of 16 g of TS-1 having the particle size distribution $D_{10}/D_{50}/D_{90}$:8.05/41.5/78.4, 20 g of a silica sol, 1.8 g of waterglass and 2.8 g of demineralized water was produced. After mixing of all substances, the resulting suspension was dispersed for 2 min at 15 000 rpm using a dispersing apparatus. After the dispersing, a particle size distribution of the suspension of $D_{10}/D_{50}/D_{90}$:6.6/43.1/77.4 was measured.

The preheated aluminum plates were then coated with this suspension at a pressure of 0.7 bar by spraying on in a plurality of steps with a spraying distance of 20 cm. A binary nozzle having a nozzle diameter of 1.8 mm was used. In the first step, a 20 μm thick layer was applied; in the subsequent steps, 40 μm thick layers were applied in each case. Thus, a catalyst layer system having a total thickness of 740 μm was produced in 18 steps. Between the steps, the plates were dried in each case for 4 min at 40° C. After the final step, the plates were dried for 12 h at 80° C.

On one plate, the catalyst system thus produced was investigated with regard to adhesive strength and topography. An orthogonal adhesive strength of 100 kPa was measured. For the roughness, an arithmetic mean roughness value of 29 μm was measured, and the tolerance of the total layer thickness was ±16 μm.

Figure 1:
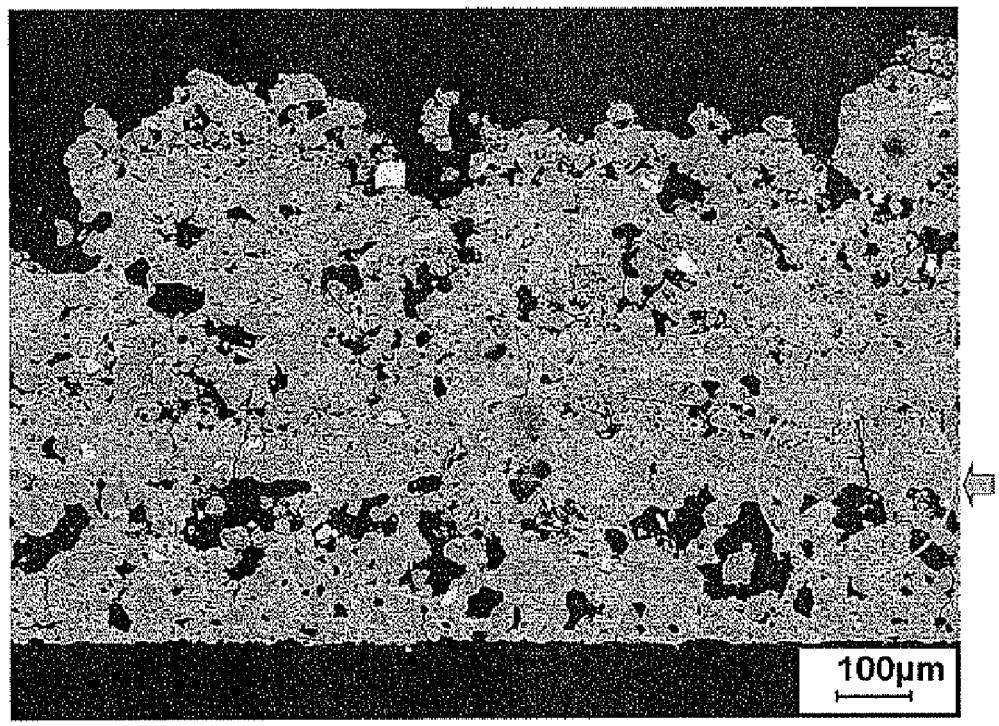
FIG. 1 depicts a micrograph of a section of a catalyst layer containing cavities.
Figure 2:
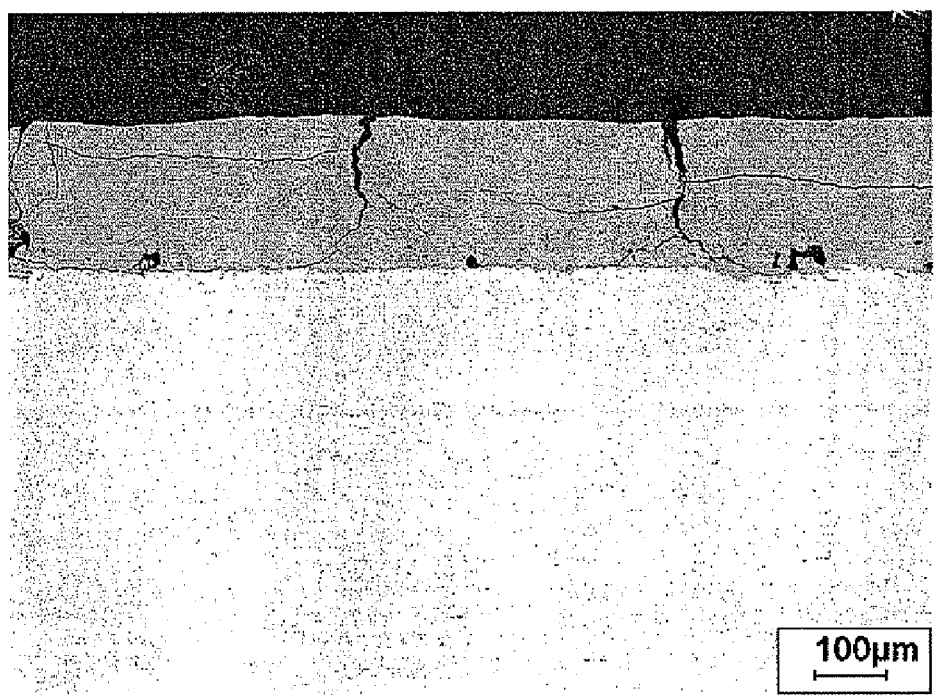
FIG. 2 depicts a micrograph of a section of a cavity-free catalyst layer.
Figure 3:
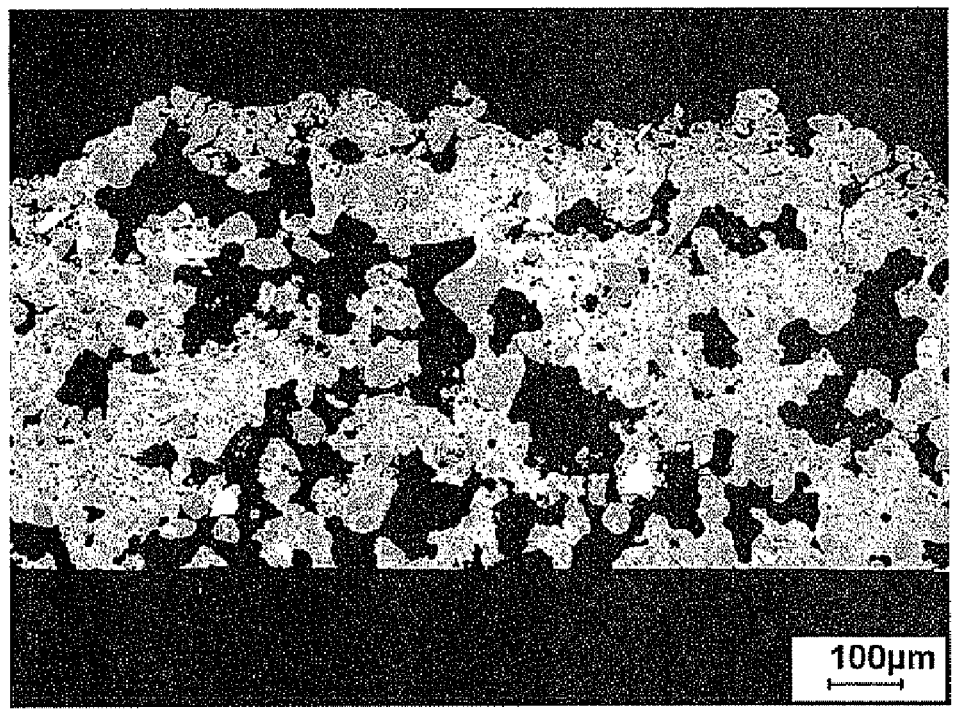
FIG. 3 depicts a sectional micrograph of a catalyst layer system produced according to Example 1.

FIG. 3 shows a sectional micrograph of a catalyst layer system produced according to this example.

The proportion of cavities of the catalyst system thus produced is 32% of the sectional area viewed in the sectional image. The pore distribution measured by means of mercury porosimetry shows that 95% of the pores have a diameter of >50 nm and the total porosity of the cavities is 49%.

Thereafter, the other two plates were installed in an experimental reactor in such a way that the grooves formed a 20 mm wide and 0.52 mm high channel. A reaction gas consisting of propene, gaseous hydrogen peroxide and nitrogen flowed through this channel in order to determine the catalytic properties of the catalyst system. This experiment was carried out at a temperature of 140° C. and a pressure of 1.2 bar over a period of 270 h. A constant propene conversion of 10% in combination with complete conversion of hydrogen peroxide was achieved. The selectivity with respect to propene oxide was 93%.

EXAMPLE 2

Wall Catalyst Pd/Au/SiO$_2$ on Stainless Steel

A 1.05 mm deep and 30 mm wide groove was cut in each case in the middle of three 400 mm long, 40 mm wide and 8 mm thick plates of stainless steel (material no. 1.4571). The webs remaining at the edges were covered with an aluminum template, and the groove to be coated was plastered with corundum at a pressure of 3 bar. After removal of the template, the plates were pickled in a solution of nitric acid and hydrofluoric acid at room temperature for 30 min and then washed neutral with demineralized water. After drying of the plates, the webs of the plates were covered with adhesive tape and preheated to 50° C.

For this catalyst system, a suspension of 37.5 g of milled catalyst, consisting of palladium, gold and silica, having a particle size distribution $D_{10}/D_{50}/D_{90}$:3.3/22.1/87.2 µm, was mixed with 31.25 g of a silica sol and 31.25 g of water and then dispersed for 2 min at 15 000 rpm using a dispersing apparatus. The particle size distribution of the suspension after the dispersing is $D_{10}/D_{50}/D_{90}$:3.8/17.2/67.0.

The preheated steel plates were coated with this suspension at a pressure of 0.8 bar by spraying on in a plurality of steps with a spraying distance of 20 cm from plate surface to spray nozzle. A binary nozzle having a nozzle diameter of 1.8 mm was used. In the first step, a 20 µm thick layer was applied; in the subsequent steps, in each case 40 µm thick layers were applied. The catalyst layer system thus produced had a total thickness of 786 µm. Between the steps, the plates were dried for 4 min at 40° C. After the final step, the plates were calcined for 6 h at 250° C.

On one plate, the catalyst system thus produced was investigated with respect to adhesive strength and topography. An orthogonal adhesive strength of >100 kPa was measured. For the roughness, an arithmetic mean roughness value of 28 µm was measured; the tolerance of the total layer thickness was ±15 µm.

Figure 4:
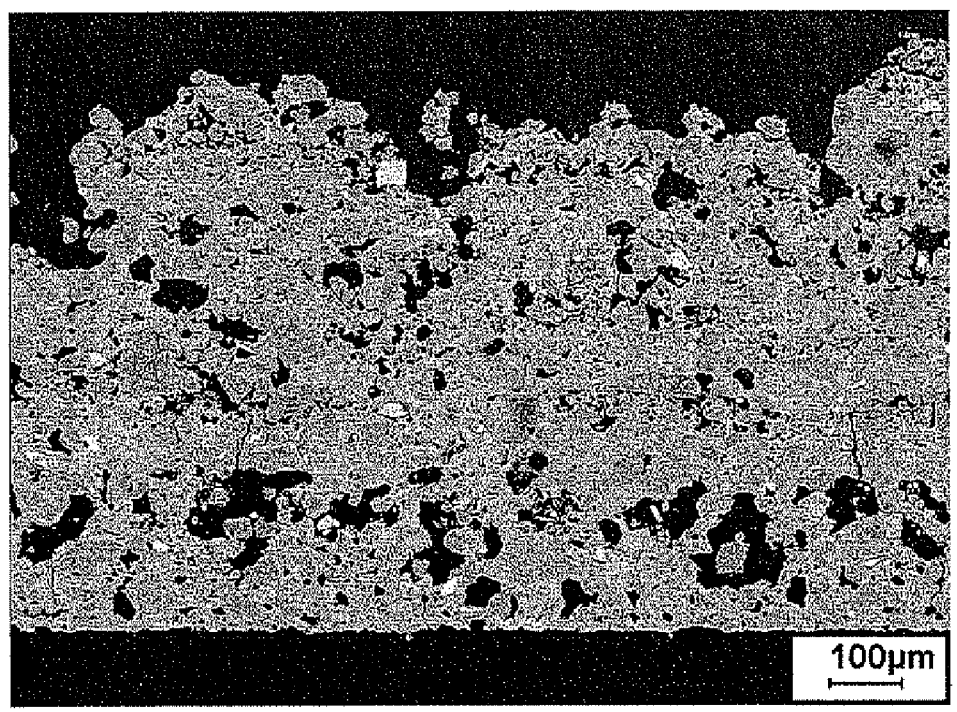
FIG. 4 depicts a sectional micrograph of a catalyst layer system produced according to Example 2.

FIG. 4 shows a sectional micrograph of the layer system produced according to this example.

Figure 5:
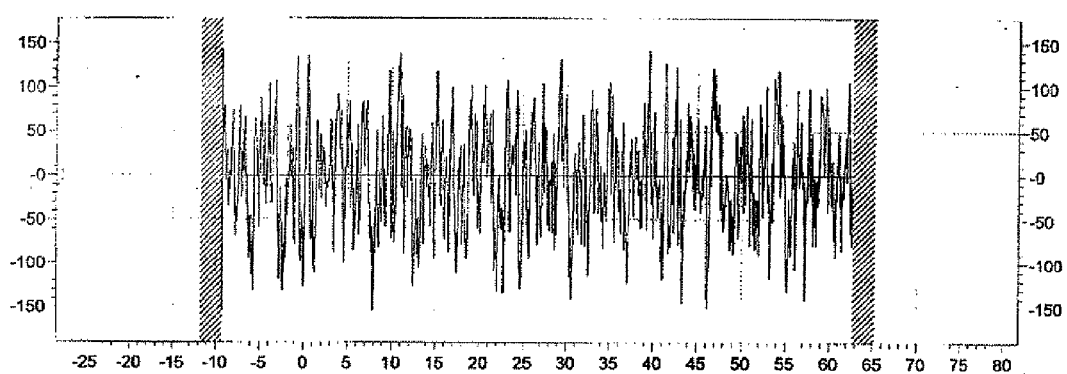
FIG. 5 depicts a profilogramme according to DIN ISO 4287 of the surface of the layer system produced according to Example 2, as determined with Form Talysurf Series 2, Taylor Hobson Precision.

FIG. 5 shows a profilogramme according to DIN ISO 4287 of the surface of the layer systems produced according to this example (determined with Form Talysurf Series 2, Taylor Hobson Precision). The abscissa shows the scan width in mm, while the ordinate shows the relative profile depth in µm.

The pore distribution measured by means of mercury porosimetry shows that 84% of the pores have a diameter of >50 nm. The total porosity with cavities is 68%

The other two plates were then installed in an experimental reactor so that their grooves formed a 0.53 mm high and 30 mm wide channel. Reaction gas consisting of ethylene, oxygen and acetic acid was passed through this channel in order to determine the catalytic property of the catalyst system. This experiment was carried out at a temperature of 155° C. and a pressure of 9 bar over a period of 180 h.

A yield of 1300 g of VAM/(kg of catalyst·h) was achieved at a selectivity of more than 95%.

EXAMPLE 3

Mixed Oxide catalyst on Stainless Steel

A 1.05 mm deep and 30 mm wide groove was cut in each case in the middle of three 400 mm long, 14 mm wide and 8 mm thick plates of stainless steel (material no. 1.4571). The webs remaining at the edges were covered with an aluminum template, and the groove to be coated was blasted with corundum at a pressure of 3 bar. After removal of the template, the plates were pickled in a solution of nitric acid and hydrofluoric acid at room temperature for 30 min and then washed neutral with demineralized water. After drying of the plates, the webs of the plates were covered with adhesive tape and preheated to 50° C.

For this catalyst system, a suspension of 37.5 g of acrolein catalyst according to EP0900774, example 1 (preparation of catalyst 2), 31.25 g of a silica sol and 31.25 g of demineralized water was prepared, and then dispersed for 2 min at 15 000 rpm using a dispersing apparatus (Ultra Turrax). The particle size distribution after the dispersing, $D_{10}/D_{50}/D_{90}$ was: 0.49/13.24/24.98. The preheated steel plates were coated with the suspension thus prepared at a pressure of 1.6 bar by spraying on in a plurality of steps with a distance of 20 cm from spray nozzle to plate surface. A binary nozzle having a nozzle diameter of 0.8 mm was used. In the first step, a layer of 20 µm was applied; in the subsequent steps, layer thicknesses of 40 µm in each case were applied by increasing the material flow at the nozzle. Between the individual steps, the plates were dried for 4 min at 50° C.; After the final step, said plates were calcined for 8 h at 450° C.

After cooling of the plates, the catalyst layers were investigated with respect to adhesive strength, topography and porosity.

An orthogonal adhesive strength of >100 kPa was measured. A mean roughness value of 25 µm in combination with a layer thickness tolerance of ±15 µm was measured. The pore distribution measured by means of mercury porosimetry showed that 76% of the pores have a diameter of >50 nm. The total porosity was 57.4%.

The invention claimed is:

1. A support having a catalytic coating comprising at least one porous catalyst layer containing cavities, said cavities being irregular spaces having dimensions greater than 5 µm in at least two dimensions or having cross-sectional areas of at least 10 µm$^2$.

2. The support of claim 1, wherein said cavities account for an area fraction of from 2 to 60%, as determined as the arithmetic mean of the area fractions in the catalyst layer of five randomly selected sectional scanning electron micrographs.

3. The support of claim 1, wherein the volume of the catalyst layer which is formed by pores and cavities is from 30 to 95%, based on the total volume of the layer.

4. The support of claim 1, wherein the thickness of said at least one catalyst layer is from 50 to 3000 µm and the variation of the layer thickness is less than 50 µm.

5. The support of claim 1, further comprising an adhesion-promoting layer which is applied directly to the surface of the support substrate and whose thickness is preferably from 100 nm to 80 µm.

6. The support of claim 5, wherein said adhesion-promoting layer has a thickness of up to 80 µm and is composed of nanoparticulate material which contains no particles having diameters of more than 5 µm.

7. The support of claim 5, wherein the material of which the particles of the adhesion-promoting layer consist are inorganic oxides and/or heat-stable plastics.

8. The support of claim 1, wherein the support substrate is a sheet-like body having sheet-like depressions on which the catalyst layers are applied, or wherein the sheet-like body has grooves in addition to sheet-like depressions.

9. The support of claim 1, further comprising porous and cavity-containing layers which consist of different or of identical material applied to a first porous and cavity-containing catalyst layer.

10. The support of claim 1, wherein said at least one porous and cavity-containing catalyst layer contains particles of catalytically active material and particles of inert binders, preferably inorganic oxides and/or heat-stable plastics.

11. The support of claim 1, wherein the catalytic coating has adhesive strengths of greater than 1 kPa, as measured according to DIN EN ISO 4624.

12. The support of claim 1, wherein measurements with the whirl pool principle according to DIN EN ISO 4287 of the thickness of the catalytic coating show standard deviations of less than 35 μm.

13. The support of claim 1, wherein the surface of the catalytic coating shows a high local roughness expressed in an average number of zero line passages of greater than 2 per mm and a roughness depth $R_z$ measured by a probe and determined according to DIN EN ISO 4287 of greater than 70 μm.

14. The support of claim 1, wherein said at least one porous and cavity-containing catalyst layer contains a catalyst from the series consisting of the molecular sieves.

15. The support of claim 1, wherein said at least one porous and cavity-containing catalyst layer contains the metals of group VIII B of the Periodic Table of the Elements combined with metals of group I B of the Periodic Table of the Elements and optionally further promoters in an oxidic support matrix.

16. The support of claim 1, wherein said at least one porous and cavity-containing catalyst layer contains the metals of group VIII B of the Periodic Table of the Elements combined with metals of group II B of the Periodic Table of the Elements and optionally further promoters in an oxidic support matrix.

17. The support of claim 1, wherein said at least one porous and cavity-containing catalyst layer contains the elements Mo, Bi, Fe, Co and Ni and optionally alkali metals as further additions.

18. The support of claim 1, wherein said at least one porous and cavity-containing catalyst layer contains the elements Mo, V, Cu and W and optionally elements of group V A of the Periodic Table of the Elements as further additions.

19. The support of claim 1, wherein said at least one porous and cavity-containing catalyst layer contains the elements Ag and optionally further additions in an oxidic support matrix.

20. The support of claim 1, wherein said at least one porous and cavity-containing catalyst layer contains vanadium pyrophosphates and optionally further additions, or contains vanadium oxide on an oxidic support and optionally further additions.

21. The support of claim 1, wherein said at least one porous and cavity-containing catalyst layer contains metals of group VIII B of the Periodic Table of the Elements in an oxidic support matrix.

22. A support having a catalytic coating comprising at least one porous catalyst layer containing cavities, said cavities being irregular spaces having dimensions greater than 5 μm in at least two dimensions or having cross-sectional areas of at least 10 μm², wherein at least 50% of the pore volume is formed by macropores having a diameter of at least 50 nm, as determined by mercury porosimetry according to DIN 66133.

23. The support of claim 22, wherein said cavities account for an area fraction of from 2 to 60%, as determined as the arithmetic mean of the area fractions in the catalyst layer of five randomly selected sectional scanning electron micrographs.

24. The support of claim 22, wherein the volume of the catalyst layer which is formed by pores and cavities is from 30 to 95%, based on the total volume of the layer.

25. The support of claim 22, wherein the thickness of said at least one catalyst layer is from 50 to 3000 μm and the variation of the layer thickness is less than 50 μm.

26. The support of claim 22, further comprising an adhesion-promoting layer which is applied directly to the surface of the support substrate and whose thickness is preferably from 100 nm to 80 μm.

27. The support of claim 26, wherein said adhesion-promoting layer has a thickness of up to 80 μm and is composed of nanoparticulate material which contains no particles having diameters of more than 5 μm.

28. The support of claim 26, wherein the material of which the particles of the adhesion-promoting layer consist are inorganic oxides and/or heat-stable plastics.

29. The support of claim 22, wherein the support substrate is a sheet-like body having sheet-like depressions on which the catalyst layers are applied, or wherein the sheet-like body has grooves in addition to sheet-like depressions.

30. The support of claim 22, further comprising porous and cavity-containing layers which consist of different or of identical material applied to a first porous and cavity-containing catalyst layer.

31. The support of claim 22, wherein said at least one porous and cavity-containing catalyst layer contains particles of catalytically active material and particles of inert binders, preferably inorganic oxides and/or heat-stable plastics.

32. The support of claim 22, wherein the catalytic coating has adhesive strengths of greater than 1 kPa, as measured according to DIN EN ISO 4624.

33. The support of claim 22, wherein measurements with the whirl pool principle according to DIN EN ISO 4287 of the thickness of the catalytic coating show standard deviations of less than 35 μm.

34. The support of claim 22, wherein the surface of the catalytic coating shows a high local roughness expressed in an average number of zero line passages of greater than 2 per mm and a roughness depth $R_z$ measured by a probe and determined according to DIN EN ISO 4287 of greater than 70 μm.

35. The support of claim 22, wherein said at least one porous and cavity-containing catalyst layer contains a catalyst from the series consisting of the molecular sieves.

36. The support of claim 22, wherein said at least one porous and cavity-containing catalyst layer contains the metals of group VIII B of the Periodic Table of the Elements combined with metals of group I B of the Periodic Table of the Elements and optionally further promoters in an oxidic support matrix.

37. The support of claim 22, wherein said at least one porous and cavity-containing catalyst layer contains the metals of group VIII B of the Periodic Table of the Elements combined with metals of group II B of the Periodic Table of the Elements and optionally further promoters in an oxidic support matrix.

38. The support of claim 22, wherein said at least one porous and cavity-containing catalyst layer contains the elements Mo, Bi, Fe, Co and Ni and optionally alkali metals as further additions.

39. The support of claim 22, wherein said at least one porous and cavity-containing catalyst layer contains the elements Mo, V, Cu and W and optionally elements of group V A of the Periodic Table of the Elements as further additions.

40. The support of claim 22, wherein said at least one porous and cavity-containing catalyst layer contains the elements Ag and optionally further additions in an oxidic support matrix.

41. The support of claim 22, wherein said at least one porous and cavity-containing catalyst layer contains vanadium pyrophosphates and optionally further additions, or contains vanadium oxide on an oxidic support and optionally further additions.

42. The support of claim 22, wherein said at least one porous and cavity-containing catalyst layer contains metals of group VIII B of the Periodic Table of the Elements in an oxidic support matrix.

* * * * *